United States Patent
Boenisch

(10) Patent No.: US 9,213,018 B2
(45) Date of Patent: Dec. 15, 2015

(54) PARTIAL SATURATION EDDY CURRENT SENSOR APPARATUS AND METHOD OF USE

(75) Inventor: Andreas Boenisch, Schwarmstedt (DE)

(73) Assignee: Innospection Group Limited (GB)

(*) Notice: Subject to any disclaimer, the term of this patent is extended or adjusted under 35 U.S.C. 154(b) by 164 days.

(21) Appl. No.: 13/509,779

(22) PCT Filed: Nov. 12, 2010

(86) PCT No.: PCT/GB2010/051892
§ 371 (c)(1),
(2), (4) Date: Aug. 21, 2012

(87) PCT Pub. No.: WO2011/058370
PCT Pub. Date: May 19, 2011

(65) Prior Publication Data
US 2012/0306483 A1 Dec. 6, 2012
US 2013/0234701 A2 Sep. 12, 2013

(30) Foreign Application Priority Data
Nov. 16, 2009 (GB) .................................. 0920005.6

(51) Int. Cl.
*G01R 33/18* (2006.01)
*G01N 27/90* (2006.01)
*G01N 27/82* (2006.01)

(52) U.S. Cl.
CPC ............ *G01N 27/9033* (2013.01); *G01N 27/82* (2013.01)

(58) Field of Classification Search
CPC ........................... G01N 27/82; G01N 27/9033
USPC .................... 324/220–221, 240–243
See application file for complete search history.

(56) References Cited

U.S. PATENT DOCUMENTS 3,205,435 A * 9/1965 Nuttall .......................... 324/220
5,237,270 A * 8/1993 Cecco et al. .................. 324/220
(Continued)

FOREIGN PATENT DOCUMENTS

DE         4118406 A1    12/1991
DE    102007004223 A1     7/2008
(Continued)

OTHER PUBLICATIONS

International Search Report and Written Opinion dated Mar. 28, 2011 from International Patent Application No. PCT/GB2010/051892 filed Nov. 12, 2010 (13 pages).
A. Boenisch: "magnetic Flux and SLOFEC Inspection of Thick Walled Components", Proc. 15th World Conference on Nondestructive Testing, Oct. 15, 2000, Oct. 21, 2000, pp. 1-8, XP002623467, Retrieved from the Internet: URL:http://www.ndt.net/article/wcndt00/papers/idn352/idn352.htm [retrieved on Feb. 17, 2011].

(Continued)

*Primary Examiner* — Jay Patidar
(74) *Attorney, Agent, or Firm* — Sunstone IP

(57) ABSTRACT

A method and apparatus for the inspection of electrically conductive components is described. The described apparatus comprises a sensor module having a magnetizer unit suitable for generating a variable DC magnetic field within the test component and an eddy current probe. The variable DC magnetic field and eddy current probe are configured to perform a partial saturation eddy current test upon the test component. The eddy current probe further comprises a magnetic field sensor that provides a means for measuring the permeability within the test component. Employing the magnetic field sensor provides apparatus that is more accurate and flexible in its modes of operation since such sensors provide a means for the actual permeability of a material being tested to be measured. The described methods and apparatus find particular application in the inspection of tubular components used in the oil and gas exploration and production industries.

20 Claims, 6 Drawing Sheets

(56) References Cited

U.S. PATENT DOCUMENTS

| | | | |
|---|---|---|---|
| 5,565,633 A * | 10/1996 | Wernicke | 73/865.8 |
| 2002/0033049 A1 | 3/2002 | Amini | |
| 2002/0093343 A1* | 7/2002 | Amini | 324/644 |
| 2003/0117142 A1* | 6/2003 | Amini | 324/339 |
| 2004/0239345 A1* | 12/2004 | Amini | 324/702 |
| 2011/0234212 A1* | 9/2011 | Lepage et al. | 324/219 |

FOREIGN PATENT DOCUMENTS

| | | |
|---|---|---|
| GB | 2187558 A | 9/1987 |
| GB | 2462193 A | 2/2010 |
| JP | 11142577 A | 5/1999 |
| JP | 2001228120 A | 2/2000 |
| WO | 02088627 A1 | 11/2002 |

OTHER PUBLICATIONS

Kontroll Technick: "SLOFEC—Saturation Low Frequency Eddy Current", Feb. 18, 2004, XP002623468, Retrieved from the Internet: URL:http://www.kontrolltechnik.com/Bilder/PDF/ProsSlofec.pdf [retrieved on Feb. 17, 2011].

Sadek H M: "NDE technologies for the examination of heat exchangers and boiler tubes-principles, advantages and limitations", Insight (Non-Destructive Testing and Condition Monitoring), British Institute of Non-Destr. Test., Northampton, GB, vol. 48, No. 3, Mar. 1, 2006, pp. 181-183, XP002486275, ISSN: 1354-2575, DOI: DOI: 10.1784/INSI.2006.48.3.181 p. 182.

* cited by examiner

PARTIAL SATURATION EDDY CURRENT SENSOR APPARATUS AND METHOD OF USE

The present invention relates to non-destructive testing, and in particular to a method and apparatus for the inspection of electrically conductive components. Applications of the invention include the inspection of tubular components used in the oil and gas exploration and production industries.

Non-destructive testing techniques are known for the detection and identification of defects and/or fatigue in the external wall of tubular components used in the oil and gas industry, such as casings, production tubing, and pipelines.

One such non-destructive testing technique known in the art is eddy current testing (ECT). ECT is based on the principle of measuring the absolute or relative impedance Z of a probe or sensor that comprises a conducting coil to which an alternating current is applied. When the alternating current is applied to the probe a magnetic field develops in and around the coil. This magnetic field expands as the alternating current rises to a maximum and collapses as the current is reduced to zero. If another electrical conductor (the apparatus to be tested) is brought into close proximity to this changing magnetic field, electromagnetic induction takes place and eddy currents (swirling or closed loops of currents that exist in metallic materials) are induced within the apparatus to be tested. The eddy Currents flowing in the test material generate their own secondary magnetic fields which oppose the primary magnetic field of the coil and thus change the impedance detected by the probe. This entire process can occur from several hundred times to several million times each second depending on the frequency of the applied alternating current.

In general, the probe is initially balanced on a defect free area of the apparatus to be tested. The probe is then moved relative to the apparatus and variations in the probe impedance Z are recorded. At regions of discontinuities (defects, material property variations, surface characteristics etc.) the flow of the eddy currents is distorted and hence a change of the impedance Z is measured by the probe.

For ECT techniques the probes can be configured in two different operational modes referred to as absolute and differential modes. Absolute probes generally have a single test coil that is used to generate the eddy currents and sense changes in the eddy current field as the probe moves over the apparatus being tested. Absolute coils are generally suited for measuring slowly varying proprieties of a material. In particular they can be used for conductivity analysis, liftoff measurements material property changes and thickness measurements.

Differential probes have two active coils usually wound in opposition. When the two coils are over a flaw-free area of test sample, there is no differential signal developed between the coils since they are both inspecting identical material. However, when one coil is over a defect and the other is over good material, a differential signal is produced. Differential probes therefore have the advantage of being very sensitive to localised defects yet relatively insensitive to slowly varying properties such as gradual dimensional or temperature variations.

ECT is an excellent method for detecting surface and near surface defects when the probable defect location and orientation is well known. However, ECT does have some inherent limitations. For example the techniques are only applicable to conductive materials, they require the surface to be tested to be accessible to the probe, and they are limited in the depth of penetration into the material being tested that can be achieved.

Partial Saturation Eddy Current Testing (PSET) is a particular type of eddy current test. PSET techniques employ conventional eddy current coils to monitor the impedance levels within a ferromagnetic material that is being tested. The eddy current coils are however located between two poles of an electromagnet and the electromagnet is arranged to apply a DC magnetic field to the material in the region being monitored by the eddy current coils. The principle behind the PSET technique is that when the ferromagnetic material is magnetised by the DC electromagnet the permeability within the material is changed. When a defect is present the magnetic field generated by the electromagnet experiences a higher flux density, analogous to the situation where a stone is placed in a river causing the water flow to divert around it. This higher flux density causes a change in the localised relative permeability and so distorts the induced eddy current fields in the material which is then detected as a change of the impedance Z measured by the probe.

PSET effectively monitors the relative change in the permeability of a material and so this technique is inherently less sensitive to gradual material property changes. It is therefore particularly effective when operated in a differential mode for the detection of localised discontinuities, such as those caused by cracks, pits and defects.

Since PSET is a relative or comparative technique, the system must be calibrated on reference samples with artificial damage and defects so as to identify the type and severity of defect. However, in practice the material of the reference sample and the test sample may be different. For example, the reference sample may have a relative permeability of 2,500 H $m^{-1}$. However the inspection pipe may have a relative permeability of 2,000 H $m^{-1}$. As a result with conventional PSET techniques the identified defect often needs to be determined or corroborated by an alternative NDT technique, for example by ultrasound testing, since the relative permeability of the pipe is usually not known. Often this is not a viable option and even when available it is time consuming and expensive.

Theoretically, PSET can also be operated within an absolute mode. However there is a known inherent problem associated with such tests. When carrying out an absolute mode PSET false hits are known to occur; i.e. a defect can be indicated when one does not truly exist. The reason for these false hits is the fact that PSET readings can be influenced by material property changes. These may include changes in electrical conductivity or changes in the grain structure, for example due to the effects of fatigue within the material. These material property changes affect the relative permeability of the material which in turn is then detected during the absolute mode PSET. The absolute mode PSET cannot however distinguish inherent material property changes from genuine problems such as wall loss. This is because the PSET does not directly measure changes in permeability, it only obtains an apparent change in permeability due the effect this has on the induced eddy currents. Thus, this apparent change could equally well be a result of a material property change or a wall loss, or indeed a combination of the two.

Theoretically, similar false readings can occur during PSET operated in a differential mode if the material property change occurs within a very localised area. However, in reality the frequency of such false readings is much lower than those described in relation to an absolute mode of operation.

One aim and object of aspects of the present invention is to provide a method and apparatus which overcomes or mitigates the drawbacks of prior art non-destructive testing techniques. A further aim and object of aspects of the invention is to provide an alternative method and apparatus to those proposed in the prior art. Additional aims and objects will become apparent from reading the following description.

SUMMARY OF INVENTION

According to a first aspect of the present invention there is provided a sensor module for the non-destructive testing of a component made of an electrically conductive material, the sensor module comprising a magnetiser unit suitable for generating a variable DC magnetic field within the test component and at least one eddy current probe wherein the sensor module is configured to perform a partial saturation eddy current test upon the test component and wherein the at least one eddy current probe comprises a magnetic field sensor that provides a means for measuring the permeability within the test component.

In the context of this description, the term partial saturation eddy current refers to an eddy current testing technique in which applied magnetic field lines are used in combination with an eddy current signal. This terminology is known in the art, but may also be referred to as magnetic biased or DC field biased eddy current testing.

The incorporation of the magnetic field sensor allows the actual permeability of a material being tested to be measured and so when used in conjunction with the magnetiser unit ensures that the permeability in the test component matches that of a calibrated standard. This reduces the reliance on alternative NDT techniques to be employed to determine or corroborate the test results obtained by the sensor module so saving on the time and costs incurred when employing the sensor module. The sensor module also offers greater flexibility in its modes of operation when compared with other apparatus known in the art. For example the incorporation of the magnetic field sensor provides a means for reducing the occurrence of false readings when the sensor module is operated within an absolute mode.

The magnetic field sensor may be integrated within the eddy current probe. With this arrangement an air gap is provided between the magnetic field sensor and the test component when the sensor module is deployed.

Most preferably the magnetic field sensor is arranged to provide a feedback signal to the magnetiser unit.

Employing the magnetic field sensor within a feedback loop to the magnetiser unit allows for the magnetic field line density within the test component to be maintained even when the distance between the sensor module and the test component varies. This provides for accurate and reproducible results to be achieved on tests performed on the components, even when they exhibit a variety of physical dimensions.

Preferably the magnetiser unit comprises a variable DC magnet source, which may be mounted between poles of a magnetic yoke.

It is preferable for the at least one eddy current probe to be positioned within the sensor module such that an air gap is provided between the eddy current probe and the test component when the sensor module is deployed.

Preferably the at least one eddy current probe is located substantially centrally between the poles of the magnetic yoke. The at least one eddy current probe, or where a plurality of probes is provided, a subset of the probes may also be flexibly supported within the sensor module in order to allow them to locate as close as possible to the test component.

Most preferably the variable DC magnetic source comprises a permanent magnet rotatably mounted with respect to the poles of the magnetic yoke. Relative rotation of the permanent magnet and the magnetic yoke therefore provides a means for varying the DC magnetic field generated within the test component.

The rotatable magnet will allow the magnetic field strength to be changed. In particular it will also allow switching off of the magnetisation such that there is no flux through the test component. This will switch off the attractive force between the sensor module and the test component. It is important for the proper handling of the sensor module that the attractive magnetic force can be switched off.

The permanent magnet may be rotatably mounted between the poles of the magnetic yoke so as to allow the permanent magnet to be moved to a deactivated position. In the deactivated position there is no, or minimal, DC magnetic field generated by the permanent magnetic within the test component.

Alternatively the variable DC magnetic source comprises an electromagnet.

The magnetiser unit may further comprise pole shoes, which may be attached to the poles of the magnetic yoke. Preferably the pole shoes are shaped so as to assist location of the sensor module with the component to be tested.

Preferably the sensor module further comprises a suspension mechanism that provides a means for varying the distance between the eddy current probes and the test component.

The sensor module may further comprise one or more distance sensors that provide a means for measuring the distance from the sensor module to a first electrically conductive layer of the test component. The distance sensors therefore provide a means for monitoring the thickness of an outer non-conductive material of the component.

The eddy current probes may comprise eddy current coils arranged to operate in a differential and/or an absolute configuration. The operating frequency range for the eddy current coils is preferably in the frequency range of 1 to 500 KHz.

Most preferably the magnetic field sensor comprises a Hall sensor. The Hall sensors preferably provide a means for measuring magnetic field strengths between about 0.1 and 0.5 Tesla.

Preferably the sensor module further comprises a data acquisition computer that provides a means for collating and analysing the signals detected by the at least one eddy current probe.

According to a second aspect of the present invention, there is provided an inspection tool system for the non-destructive testing of components made of an electrically conductive material the inspection tool system comprising at least one sensor module in accordance with the first aspect of the present invention.

According to a third aspect of the present invention there is provided a method for the non-destructive testing of an electrically conductive test component, the method comprising:
  measuring a permeability within the electrically conductive test component;
  varying the strength of a DC magnetic field generated within the electrically conductive test component until the measured permeability corresponds to a predetermined value; and
  performing a Partial Saturation Eddy Current test upon the test component to evaluate a condition of the test component.

The incorporation of the step of measuring the permeability within the electrically conductive component allows the strength of the generated DC magnetic field within the electrically conductive test component to be set so that the permeability within the test component matches that of a calibrated standard. This reduces the reliance on alternative NDT techniques to be employed to determine or corroborate the test results obtained by the sensor module so saving on the time and costs incurred when employing the described method.

Most preferably the method for the non-destructive testing of electrically conductive components further comprises the step of automatically varying the strength of the DC magnetic field generated in response to a feedback signal from the measured permeability within the electrically conductive component.

Employing a feedback signal of the measured permeability to the generated DC magnetic field allows for the magnetic field line density and hence the permeability within the component to be maintained throughout the duration of a test. This provides for accurate and reproducible results to be achieved on tests performed on the components, even when they exhibit a variety of physical dimensions.

Optionally the feedback signal is employed to control the orientation of a permanent magnet with respect to poles of a permanent magnetic yoke. Alternatively the feedback signal is employed to control the current provided to an electromagnet, which may be located between poles of a permanent magnetic yoke.

Optionally the step of performing the Partial Saturation Eddy Current test upon the component comprises performing an absolute mode Partial Saturation Eddy Current test. In this embodiment, when the Partial Saturation Eddy Current test detects a defect a cross reference is made with the measured permeability within the test component so as to determine whether the detected defect is a result of a material change within the test component. Employing this cross reference check reduces the occurrence of false readings of defects being detected.

Alternatively the step of performing the Partial Saturation Eddy Current test upon the component comprises performing a differential mode Partial Saturation Eddy Current test.

The method may comprise the additional step of selecting or rejecting the test component for further use according to the evaluated damage condition. Alternatively, the method may comprise classifying the test component according to the evaluated damage condition.

The test component may be rejected if a predetermined measured value is exceeded in the Partial Saturation Eddy Current test.

Preferably, the method further comprises the additional step of generating a report on the condition of a test component. The method may comprise the additional step of using the evaluation of the condition of a test component to generate a display to a user. The method may comprise the additional step of using the evaluation of the condition to create an image of the condition of the test component and displaying the image to a user.

According to a fourth aspect of the present invention there is provided a method for the non-destructive testing of an electrically conductive test component, the method comprising:
  measuring a permeability within the electrically conductive test component;
  performing a Partial Saturation Eddy Current test upon the test component to evaluate a condition of the test component; and
  automatically varying the strength of a DC magnetic field generated for performing the Partial Saturation Eddy Current test in response to a feedback signal from the measured permeability within the electrically conductive component.

Employing a feedback signal of the measured permeability to the generated DC magnetic field allows for the magnetic field line density and hence the permeability within the component to be maintained throughout the duration of a test. This provides for accurate and reproducible results to be achieved on tests performed on the components, even when they exhibit a variety of physical dimensions.

Optionally the method further comprises the step of initially varying the strength of the DC magnetic field generated within the electrically conductive test component until the measured permeability corresponds to a predetermined value.

Embodiments of the fourth aspect of the invention may comprise preferable or optional steps of the method of the third aspects of the invention or preferable or optional features of the first or second aspects of the invention, or vice versa.

According to a fifth aspect of the present invention there is provided a sensor module for the non-destructive testing of a component made of an electrically conductive material, the sensor module comprising a magnetiser unit suitable for generating a variable DC magnetic field within the test component and at least one eddy current probe wherein the variable DC magnetic field and eddy current probe are configured to perform a partial saturation eddy current test upon the test component and wherein the at least one eddy current probe comprises a magnetic field sensor that provides a means for measuring the permeability within the test component.

Embodiments of the fifth aspect of the invention may comprise preferable or optional steps of the method of the third or fourth aspects of the invention or preferable or optional features of the first or second aspects of the invention, or vice versa.

According to a sixth aspect of the present invention there is provided a method for the non-destructive testing of an electrically conductive test component, the method comprising:
  measuring a permeability within the electrically conductive test component;
  varying the strength of a DC magnetic field generated within the electrically conductive test component until the measured permeability corresponds to a predetermined value; and
  employing the variable DC magnetic field to perform a Partial Saturation Eddy Current test upon the test component to evaluate a condition of the test component.

Embodiments of the sixth aspect of the invention may comprise preferable or optional steps of the method of the third or fourth aspects of the invention or preferable or optional features of the first, second or fifth aspects of the invention, or vice versa.

BRIEF DESCRIPTION OF DRAWINGS

Aspects and advantages of the present invention will become apparent upon reading the following detailed description and upon reference to the following drawings in which.

DETAILED DESCRIPTION

Figure 1:
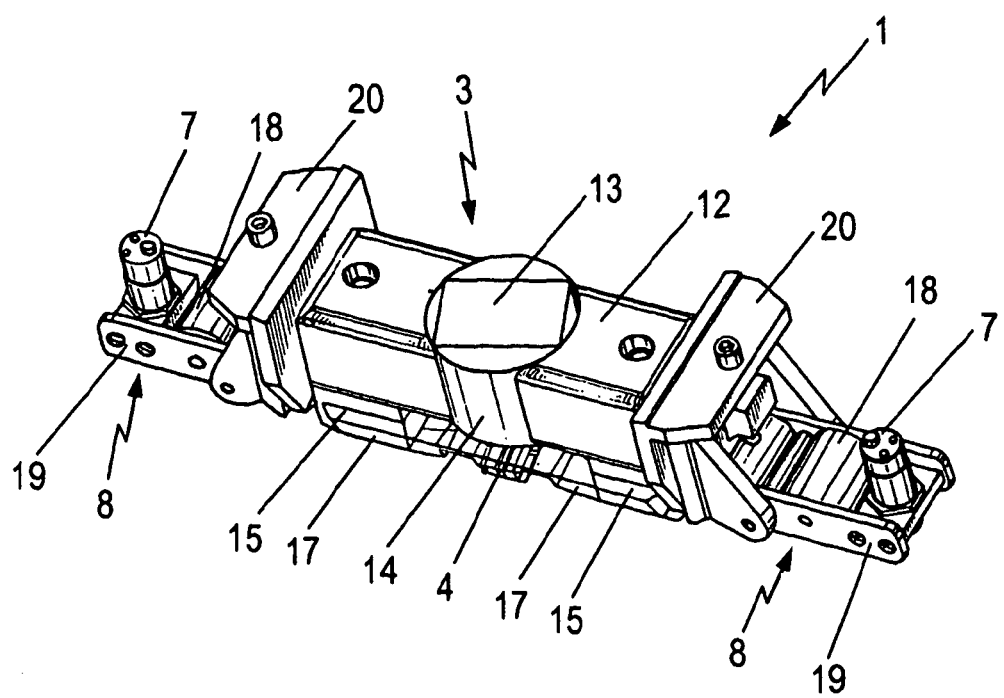
FIG. 1 presents a perspective view of a sensor module in accordance with an embodiment of the invention.
Figure 2:
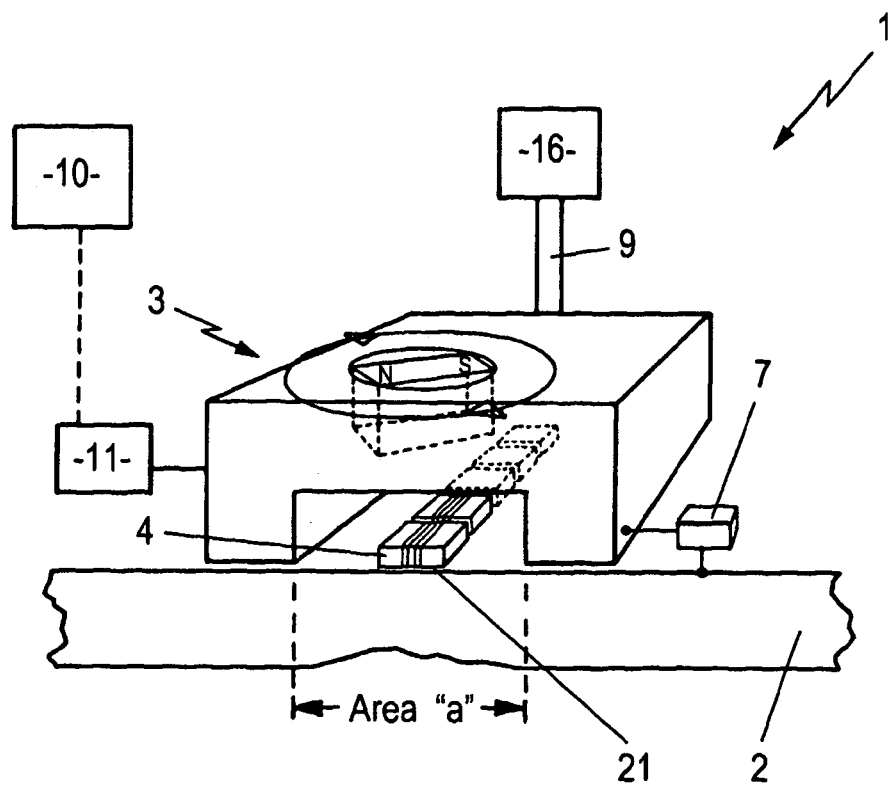
FIG. 2 presents a schematic representation of the sensor module of FIG. 1.

FIG. 1 presents a perspective view of a sensor module 1 in accordance with an embodiment of the invention while FIG. 2 presents a schematic representation of the sensor module 1 located with a component to be tested 2. The sensor module 1 can be seen to comprise a DC magnetiser unit 3, an array of eddy current probes 4, each eddy current probe 4 comprising an eddy current coil 5 with an integrated magnetic field sensor 6 e.g. a Hall sensor, one distance sensor 7 and two suspension wheel mechanisms 8. Electronic connectors 9 are employed to provide power to the sensor module 1 e.g. for the DC magnetiser unit 3, the eddy current coils 5, the Hall sensors 6 etc.

Signals detected by the sensor module 1 are transmitted to a data acquisition computer 10 that is employed to record all of the eddy current and Hall sensor data. The computer 10 may form an integrated part of the sensor module 1 or be located remotely. Transmission of the data may be via hard-wiring e.g. via a fibre optic line or by wireless transmission techniques. A multiplexer board 11 may be incorporated within the sensor module 1 so as to provide a means for multiplexing the data from all of the eddy current coils 5 and the integrated Hall sensors 6 in the array to respective channels of the data acquisition computer 10.

The magnetiser unit 3 comprises a permanent magnetic yoke 12 through which the magnetic flux strength can be adjusted. To achieve this, the magnetiser unit 3 has a permanent magnet 13 located within a rotatable cylindrical barrel 14 that is positioned between the poles 15 of the permanent magnetic yoke 12. Controlled rotation of the cylindrical barrel 14 is provided by an electric motor 16 which is itself preferably controlled by the data acquisition computer 10.

By rotating the permanent magnet 13 in the cylindrical barrel 14, the magnetic field lines can be arranged to be directed through the poles 15 (when the permanent magnet 13 lies perpendicular to the orientation of the poles 15) or to be directed parallel to the poles 15 (when the permanent magnet lies parallel to the orientation of the poles 15). Thus the magnetiser unit 3 can be moved between a fully activated position and a deactivated position, respectively.

Rotation of the permanent magnet 13 between the fully activated position and the deactivated position allows for the DC magnetic field strength generated by the magnetiser unit 3 to be varied. During operation the position of the permanent magnet 13, and hence the strength of the magnetic field produced by the magnetiser unit 3, is controlled automatically by the motor 16 in conjunction with feedback from the Hall sensors 6 (as described in further detail below)

It will be appreciated by those skilled in the art that the magnetiser unit 3 may comprise a DC electromagnet instead of the combination of the permanent magnet 13 mounted and the cylindrical barrel 14.

Located underneath the poles 15, may be fitted pole shoes 17 that are preferably shaped to locate with the component 2 to be tested. For example, the pole shoes 17 may exhibit a curved profile that assists the location of the sensor module 1 upon the outer surface of a pipe.

At either end of the magnetiser unit 3 are located the suspension wheel mechanisms 8. Each suspension wheel mechanisms 8 comprise a pair of rollers 18 mounted upon an adjustable arm 19. The suspension wheel mechanisms 8 therefore provide a means for varying the distance between the eddy current probes 4 and the test component 2. The positional adjustment is provided by means of two lift-off adjustment mechanism 20. In the presently described embodiment the lift-off adjustment mechanism comprises a screw mechanism that allows the distance to be increased or decreased, as appropriate.

The distance sensor 7, which may be inductive or capacitive type sensors, are located on the adjustable arms 19. The distance sensor 7 provides a means for measuring the distance to the first metallic layer of the component 2 to be tested. Thus, if the component 2 comprises an outer non-conductive material e.g. polyethylene, then the distance sensor 7 provides a means for monitoring its thickness. This information provides valuable details of the outer plastic coatings e.g. polyethylene incorporated within components used in the oil and gas exploration and production industries. In addition, the measured distance to the first outer ferromagnetic layer helps determine the actual distance between the eddy current probes 4 and the test component 2. It will be appreciated by those skilled in the art that alternative embodiments of the sensor module 1 may comprise a single distance sensor 7.

The sensor module 1 is arranged such that the array of eddy current probes 4 are located centrally between the poles 15, and if present, the pole shoes 17 of the magnetiser unit 3. In a preferred embodiment the Hall sensors 6 comprise chips embedded within the eddy current probes 4. Alternatively the eddy current probes 4 may be retracted from the plane defined by the poles 15 the permanent magnetic yoke 12 and optionally flexibly supported in order to run as close as possible to the surface of the component 2 to be tested. With both of these arrangements an air gap 21 is provided between the eddy current probes 4 and the component 2 when the sensor module 1 is deployed. As a result the Hall sensors 6 provide a means for measuring magnetic field strength within the air gap 21. Measuring the axial magnetic field component within the air gap 21 allows for the determination of the magnetisation levels within the test component 2. This is because the parallel component of the magnetic field is continuous. The larger the air gap 21 however the more difficult it is to determine the magnetisation levels within the test component 2. This unique relation is such that if the Hall sensors 6 are calibrated for a certain magnetisation levels then the Hall sensors 6 allow for an operator to determine when the same level of magnetisation is reached within the test component 2.

The eddy current coils 5 may comprise a Bridge coil system operated in a differential and/or an absolute configuration or a send-receive coil system operated in a differential and/or an absolute configuration. The operating frequency range for the eddy current coils 5 is preferably in the frequency range of 1 to 500 KHz while the Hall sensors 6 preferably provide a means for measuring magnetic field strengths between 0.1 and 0.5 Tesla. These magnetic field strengths correspond to magnetisations levels of up to 1.6 T within the test component itself.

Operation of the Sensor Module

Figure 3:
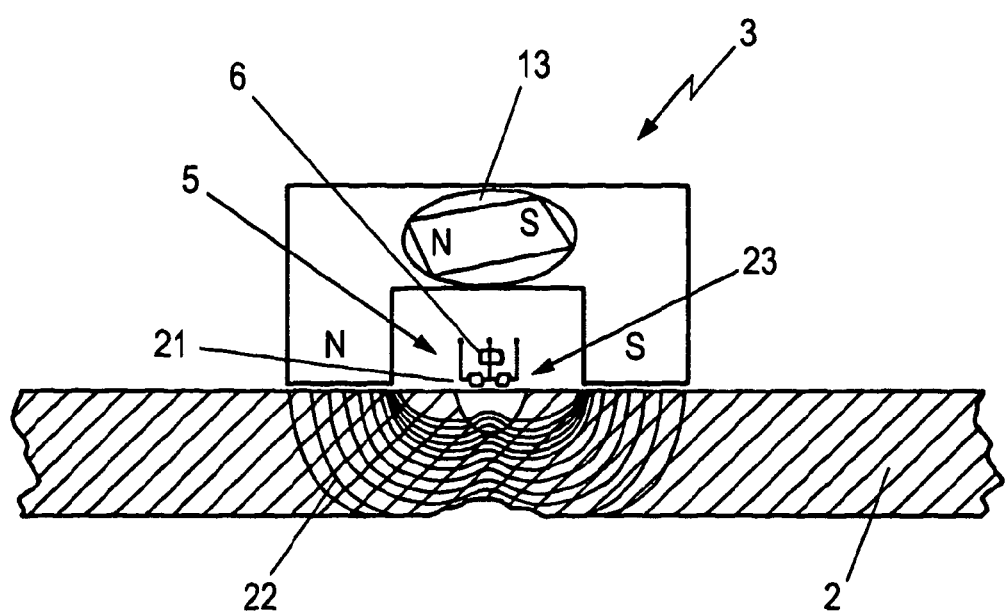
FIG. 3 presents a second schematic representation of the sensor module of FIG. 1 indicating the eddy currents and magnetic field lines present during operation.

The principles of operation of the sensor module 1 will now be described with reference to FIG. 3. In particular, FIG. 3 shows the magnetic field line density 22 of the magnetic field generated by the magnetiser unit 3 and the eddy currents 23 generated in the test component 2 by the alternating current flowing through the eddy current coils 5. The basic steps in performing an inspection with the sensor module 1 are as follows:

employing the sensor module 1 to measure the permeability within the electrically conductive test component 2;

varying the strength of a DC magnetic field generated within the electrically conductive test component 2 until the measured permeability corresponds to a predetermined value; and performing a Partial Saturation Eddy Current test upon the test component 2 to evaluate a condition of the test component.

The first step generally employs the selecting a frequency and strength for the AC current to drive the eddy current coils 5 so as to provide the most suitable combination for testing of the component 2. The Hall sensors 6 are then employed to measure the permeability within the electrically conductive test component 2

The Hall sensors 6 are again employed in the step of varying the strength of the DC magnetic field generated within the electrically conductive test component 2. Since the sensor module 1 is initially calibrated with a reference sample the Hall sensors 6 can be employed to measure the magnetic field line density 22 and, as described above, effectively provides a measurement of the permeability within this reference sample. Therefore, when the sensor module 1 is located on a defect free area of the test component 2 the DC magnetic field produced by the magnetiser unit 3 can be varied until the magnetic field line density 22, and hence the permeability within the test component 2, mirrors that used during calibration process. Since the permeability within the calibration sample and the test component are now set to be one to one, then the influence of a defect on the eddy currents 23 will be the same. The employment of the Hall sensors 6 therefore provides a means for consistently reproducing results between the calibration sample and the test components 2. This removes the need for alternative NDT techniques to be employed to determine or corroborate the test results and so the time and costs incurred when employing the sensor module 1 to carry out a NDT is significantly reduced.

The step of performing the Partial Saturation Eddy Current test generally involves the steps of scanning the sensor module 1 over the surface of the test component 2 so as to monitor the impedance signal detected by the eddy current coils 5 and the magnetic field strength signals detected by the Hall sensors 6. The signal detected by the eddy current coils 5 indicated the presence of defects and both signals can thereafter be analysed so as to identify the type of defects detected.

A further advantage of employing the Hall sensors 6 within the sensor module 1 is that they provide a means for maintaining the appropriate magnetic field line density 22, and hence the permeability, within the test component 2 for the duration of a scan. In reality test components 2 often comprise bends exhibiting various radii of curvature. As a result it can be difficult to maintain the thickness of the air gap 21 as the module 1 is scanned over the test component 2. Other factors which can alter the distance between the sensor module 1 and the test component 2 include variations in the thicknesses of an outer non-conductive material. If the distance between the sensor module 1 and the test component 2 increases the magnetic field line density 22 within the test component 2 will reduce. In a similar manner, if the distance between the sensor module 1 and the test component 2 decreases then the magnetic field line density 22 within the test component 2 will be increased. In order to maintain the permeability within the test component 2 the magnetic field strength needs to be increased or decreased, as appropriate.

With normal PSET apparatus it is not possible to determine the level by which the magnetic field strength should be increased or decreased. However the Hall sensors 6 provide the means for achieving this functionality since they provide a measurement of the permeability within the test component 2 and so can be employed as a feedback to the magnetiser unit 3. In this way the magnetic field line density 22 can be automatically monitored and controlled by the Hall sensors 6 and the magnetiser unit 3 so as to maintain the required level permeability within the test component 2. Thus the sensor modules 1 can be employed with test components 2 having a variety of physical dimensions without any noticeable reduction in the accuracy of the results obtained.

A further advantage of the incorporation of the Hall sensors 6 is in their ability to reduce the occurrence of false readings, particularly within the embodiments of the sensor module 1 that employ probes comprising absolute coils. For example, consider the situation where the eddy current signal 23 detects an apparent change in permeability. As discussed previously, this apparent change in permeability may be due to wall loss or to a material changes within the test component 2. The Hall sensors 6 provide an alternative means for detecting permeability changes which result from change in the material properties itself e.g. electrical conductivity or changes in the grain structure, due to the effects of fatigue within the material. By using the results obtained from the Hall sensors 6 as a cross reference with those detected by the eddy current coils 5 those permeability changes due to inherent material changes can be eliminated during the analysis process.

It will be appreciated by those skilled in the art that one or more of the above described sensor modules 1 may be incorporated within an inspection tool system employed for the non-destructive testing of components made of an electrically conductive material.

Figure 4:
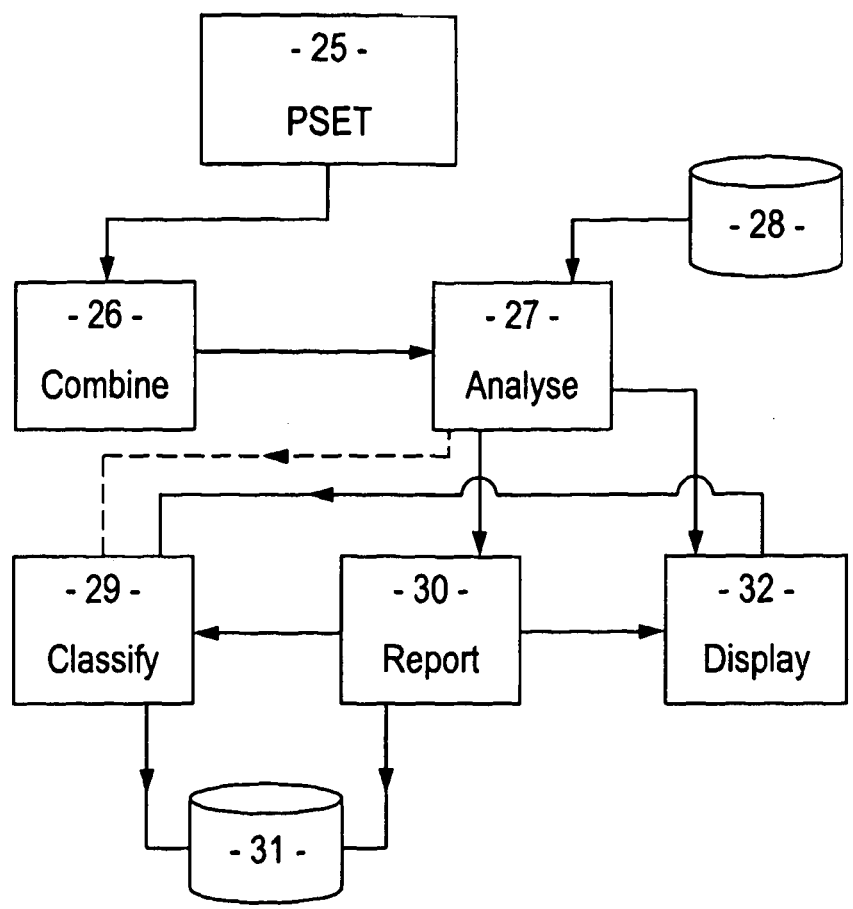
FIG. 4 presents a block diagram schematically showing the interaction of components of the apparatus of FIG. 1 in overview.

FIG. 4 shows schematically the interaction 24 of different components of such an inspection tool. At step 25, once the Hall sensor 6 has been employed in conjunction with the magnetiser unit 3 to set the required permeability within the test component 2 the partial saturation eddy current test is performed. Test are carried out over a surface area of the test component 2 and the measured data is combined at step 26 in the data acquisition computer 10. At step 27, the data are analysed in the data acquisition computer 10 and are compared with calibration data held in database 28. The results of this analysis may be used to directly classify (step 29) the test component 2, for example indicating that it is suitable or unsuitable for a particular application. Alternatively, the classification step 29 may be based on a report at step 30. The report may be written to a database at step 31. In addition, at step 32, a display may be generated from the report, for display to a user. The user, who may be an expert in non-destructive testing and NDT test data interpretation, may then classify the test component 2 based on their interpretation of the data. Alternatively, the expert user may confirm or verify an automatic classification performed by the inspection tool. The results of the classification may be stored along with the report data and details of the test component 2 or particular oil and gas installation tested.

Figure 5:
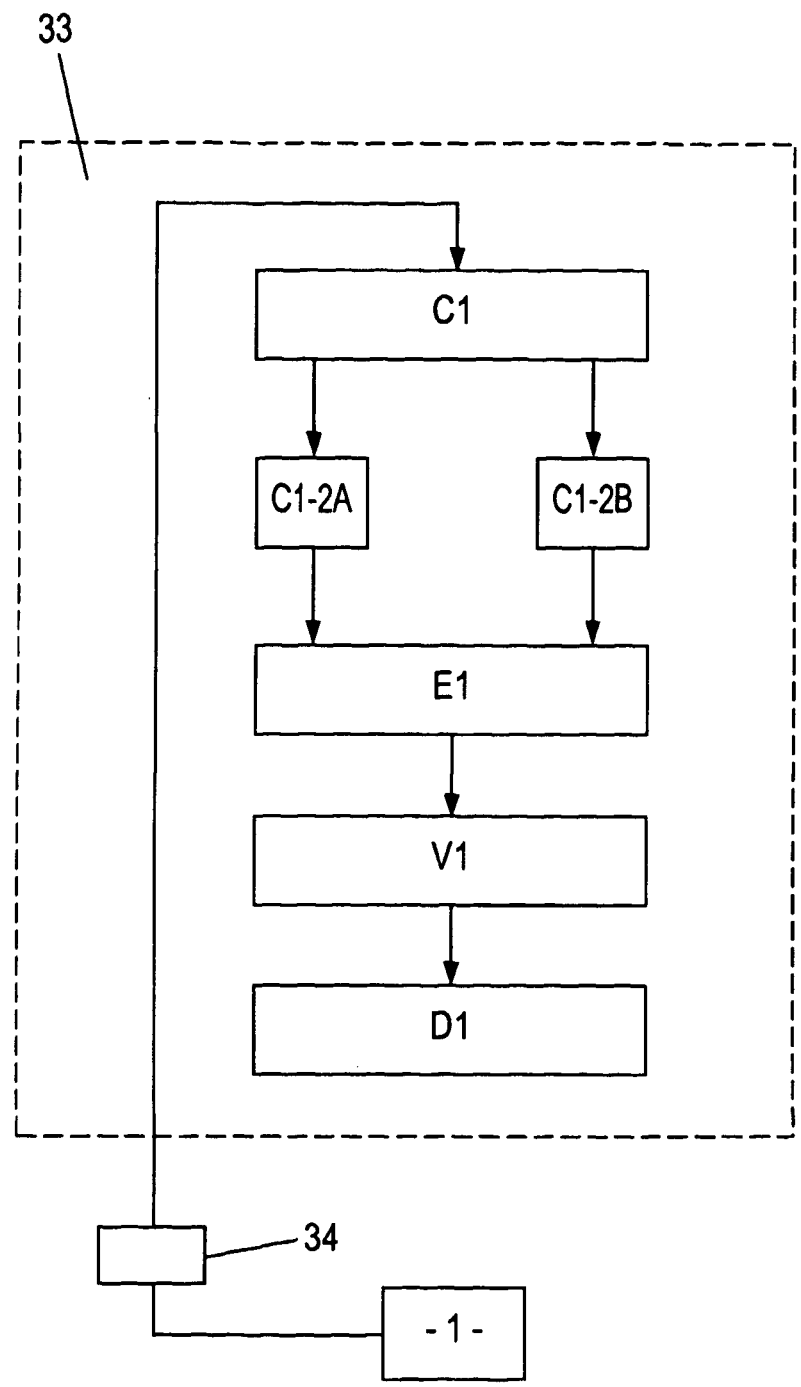
FIG. 5 is block diagram of a processing system in accordance with an embodiment of the invention.
Figure 6:
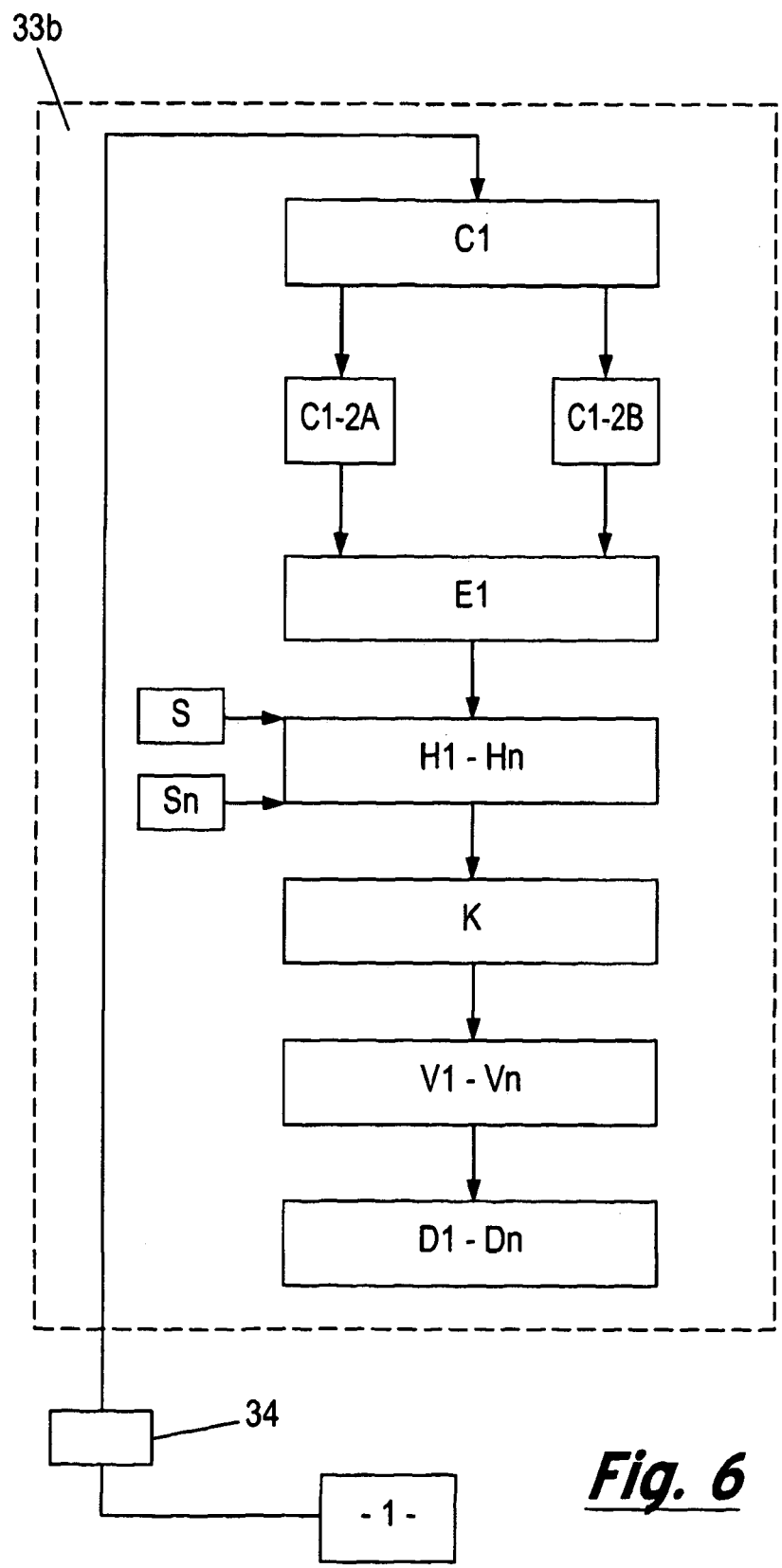
FIG. 6 is block diagram of a processing system in accordance with an alternative embodiment of the invention.

FIGS. 5 and 6 are flow charts which show the processing of the measurement data according to example embodiments of the invention. In these embodiments, the data processing module 33 is located within the data acquisition computer 10 which is located remotely from the sensor modules 1, and is configured to receive the data transmitted by the sensor modules 1 via a fibre optic interface 34.

In the example of FIG. 5, the measurement data are received in the data processing module 33 from the fibre optic interface 34 and multiplexer board 11. In step C1 the partial saturation eddy current measurement data are received in the data processing module 33, and the signal phase (step C1-2A) and the signal amplitude (step C1-2B) are evaluated individually. The analysing algorithm uses in step C1-2A the signal phase to characterise a type of event which has been detected in the wall of the component 2, and uses in step C1-2B signal amplitude as a representation of the order of magnitude of a detected event. The results are indicated at evaluation step E1.

This comparison with calibration data held in database 28 takes place at step V1, and may be used directly to provide an assessment of the condition of the test component 2. The result of the comparison is recorded in data storage means at step D1.

An alternative processing method is shown schematically in FIG. 6 of the drawings, and is also carried out while using the sensor module 1 in data processing module 33b. The embodiment of FIG. 6 is similar to that of FIG. 5, with like steps indicated with like reference numerals. However, the embodiment of FIG. 6 differs in that provision is made for an additional evaluation of the test component 2 by the use of predetermined quality criteria which are preset into the system as analysis thresholds. An appropriate number of analysis thresholds S1 to Sn are preset in the data processing module 33b. At step H1 to Hn, the evaluation results E1 are compared with the analysis thresholds. A signal indication is output at step K, for example if the analysis threshold has been exceeded, and indicates that the test object should be rejected. In step V1-Vn, a visual indication is presented to an operator, and step D1 to Dn, the analysis results are recorded in the data storage module 31. In this embodiment, the results of the evaluation steps E1 may optionally be visually (and/or audibly) presented to the operator at steps V1-Vn.

In the method of FIG. 6, the inspection tool is calibrated before use, by using calibrating test objects. These calibrating test objects are of substantially the same dimensions and materials as the components to be inspected. The calibration test objects comprise artificially-produced instances of damage to the material with known dimensions. In a preferred embodiment, the calibration defects are made according to international standards, such as the specifications of the American Petroleum Institute (API). The test defects may for example be produced by spark erosion, machining or drilling. By using calibrated test objects, the sensitivity of the tool system to the kind of defects which are typically encountered can be verified. After calibration to the API standards, the inspection tool may be used for the inspection of components, including tubular components used in the oil and gas exploration and production industries.

The described sensor module provides a number of significant advantages over the apparatus and methods known in the art. In the first instance the incorporation of the Hall sensors provides NDT apparatus that is more accurate and flexible in its modes of operation since their employment provide a means for the actual permeability of a material being tested to be measured. As a result the Hall sensors can be used in conjunction with the magnetiser unit so as to ensure that the permeability in a test component matches that of the calibrated standard. This removes the need for alternative NDT techniques to be employed to determine or corroborate the test results obtained by the sensor module so saving on the time and costs incurred when employing the described apparatus. Indeed there are often environments where such alternative NDT apparatus cannot be deployed and so in these circumstances determination or corroboration would simply not be available.

Secondly the use of the Hall sensors within a feedback loop to the magnetiser unit allows for the magnetic field line density within a test component to be maintained even when the distance between the sensor module and the test component is altered. This provides for more accurate and reproducible results on the test components, even when they exhibit a variety of physical dimensions, when compared with results obtained from NDT apparatus known in the art.

The described sensor module also offers greater flexibility in its modes of operation when compared with other apparatus known in the art. For example the incorporation of the Hall sensors provides a means for reducing the occurrence of false readings, particularly when the sensor module is operated within an absolute mode. Thus the described apparatus and methods can be accurately employed in both absolute and differential mode of operation. The described apparatus and methods may therefore be readily deployed for the non-destructive testing of ferromagnetic materials in the form of single or multiple layer structures e.g. pipes, plates, vessels (tank floors, vessel plating), steel bridge structures, flexible risers and steel wire ropes (including power wires).

The invention provides a sensor module comprising a magnetiser unit for generating a variable DC magnetic field and an eddy current probe is described. The apparatus provides a means for performing partial saturation eddy current tests upon a test component. A magnetic field sensor is incorporated within the eddy current probe thus allowing for the permeability within the test component to be measured. The permeability within the test component can therefore be matched to that of a calibrated standard so reducing the reliance on alternative non-destructive testing techniques to be employed to determine or corroborate the test results. The magnetic field sensor may also be arranged to provide a feedback signal to the magnetiser unit thus allowing the magnetic field line density within the test component to be maintained during a test. Accurate and reproducible results can therefore be achieved on test components exhibiting a variety of physical dimensions.

A method and apparatus for the inspection of electrically conductive components is described. The described apparatus comprises a sensor module having a magnetiser unit suitable for generating a variable DC magnetic field within the test component and an eddy current probe. The variable DC magnetic field and eddy current probe are configured to perform a partial saturation eddy current test upon the test component. The eddy current probe further comprises a magnetic field sensor that provides a means for measuring the permeability within the test component. Employing the magnetic field sensor provides apparatus that is more accurate and flexible in its modes of operation since such sensors provide a means for the actual permeability of a material being tested to be measured. The described methods and apparatus find particular application in the inspection of tubular components used in the oil and gas exploration and production industries.

The foregoing description of the invention has been presented for purposes of illustration and description and is not intended to be exhaustive or to limit the invention to the precise form disclosed. The described embodiments were chosen and described in order to best explain the principles of the invention and its practical application to thereby enable others skilled in the art to best utilise the invention in various embodiments and with various modifications as are suited to the particular use contemplated. Therefore, further modifications or improvements may be incorporated without departing from the scope of the invention as defined by the appended claims.

The invention claimed is:

1. A partial saturation eddy current sensor module for the non-destructive testing of a test component made of an electrically conductive material, the sensor module comprising a magnetiser unit generating a variable DC magnetic field within the test component and at least one eddy current probe, wherein the sensor module performs a partial saturation eddy current test upon the test component, wherein the at least one eddy current probe comprises a magnetic field sensor that provides a means for measuring the permeability within the test component, wherein the magnetic field sensor provides a feedback signal to the magnetiser unit.

2. A sensor module as claimed in claim 1 wherein the magnetiser unit comprises a variable DC magnet source.

3. A sensor module as claimed in claim 2 wherein the variable DC magnet source is mounted between poles of a magnetic yoke.

4. A sensor module as claimed in claim 3 wherein the at least one eddy current probe is located substantially centrally between the poles of the magnetic yoke.

5. A sensor module as claimed in claim 2 wherein the variable DC magnetic source comprises a rotatably mounted permanent magnet.

6. A sensor module as claimed in claim 5 wherein the rotatably mounted permanent magnet is rotatably mounted with respect to the poles of the magnetic yoke.

7. A sensor module as claimed in claim 6 wherein the permanent magnet is rotatably mounted between the poles of the magnetic yoke so as to allow the permanent magnet to be moved to a deactivated position.

8. A sensor module as claimed in claim 6 wherein the magnetiser unit further comprise pole shoes attached to the poles of the magnetic yoke.

9. A sensor module as claimed in claim 8 wherein the pole shoes are shaped so as to assist location of the sensor module with the component to be tested.

10. A sensor module as claimed in claim 1 wherein the at least one eddy current probe is positioned within the sensor module such that an air gap is provided between the eddy current probe and the test component when the sensor module is deployed.

11. A sensor module as claimed in claim 10 wherein the magnetic field sensor is integrated within the eddy current probe.

12. A sensor module as claimed in claim 1 wherein at least one of the eddy current probes is flexibly supported within the sensor module in order to allow them to locate as close as possible to the test component.

13. A sensor module as claimed in claim 1 wherein the magnetiser unit comprises an electromagnet.

14. A sensor module as claimed in claim 1 wherein the sensor module further comprises a suspension mechanism that provides a means for varying the distance between the eddy current probes and the test component.

15. A sensor module as claimed in claim 1 wherein the sensor module further comprises one or more distance sensors that provide a means for measuring the distance from the sensor module to a first electrically conductive layer of the test component.

16. A sensor module as claimed in claim 1 wherein the eddy current probes comprise eddy current coils arranged to operate in a differential configuration.

17. A sensor module as claimed in claim 1 wherein the eddy current probes comprise eddy current coils arranged to operate in an absolute configuration.

18. A sensor module as claimed in claim 1 wherein the magnetic field sensor comprises a Hall sensor.

19. A sensor module as claimed in claim 1 wherein the sensor module further comprises a data acquisition computer that provides a means for collating and analysing the signals detected by the at least one eddy current probe.

20. An inspection tool system for the non-destructive testing of test components made of an electrically conductive material the inspection tool system comprising at least one sensor module as claimed in claim 1.

* * * * *